US United States Patent [19] [11] 3,959,471
Hardtmann et al. [45] May 25, 1976

[54] 4,6-DIARYL-PYRIMIDIN-2(1H)-ONES AS TRANQUILIZERS

[75] Inventors: Goetz E. Hardtmann, Florham Park; Faizulla G. Kathawala, West Orange, both of N.J.

[73] Assignee: Sandoz, Inc., E. Hanover, N.J.

[22] Filed: Mar. 24, 1975

[21] Appl. No.: 561,486

Related U.S. Application Data

[60] Division of Ser. No. 385,402, Aug. 3, 1973, Pat. No. 3,892,860, which is a division of Ser. No. 172,583, Aug. 17, 1971, Pat. No. 3,772,272, which is a continuation-in-part of Ser. No. 37,341, May 14, 1970, abandoned, which is a continuation-in-part of Ser. No. 878,575, Nov. 20, 1969, abandoned.

[52] U.S. Cl. ............................................. 424/251
[51] Int. Cl.$^2$ ................................... A61K 31/505
[58] Field of Search ................................... 424/251

[56] References Cited
OTHER PUBLICATIONS
Chem. Abst. 69-77211b 1968.

*Primary Examiner*—Stanley J. Friedman
*Attorney, Agent, or Firm*—Gerald D. Sharkin; Richard E. Vila

[57] ABSTRACT

The invention discloses compounds of the class of 1-substituted-4,6-diaryl-pyrimidin-2(1H)-ones, e.g. 1-alkyl-4,6-diphenyl-pyrimidin-2(1H)-ones. The disclosure also includes the preparation of the pyrimidin-2(1H)-ones by oxidation of the corresponding dihydro derivatives and by cyclization of a dibenzoylmethane with an N-alkyl-urea. Utility as pharmaceutical agents such as tranquilizers, sleep-inducers and anti-inflammatory agents is also disclosed.

5 Claims, No Drawings

4,6-DIARYL-PYRIMIDIN-2(1H)-ONES AS TRANQUILIZERS

This application is a division of copending application Ser. No. 385,402, filed Aug. 3, 1973 and now U.S. Pat. No. 3,892,860, which is a division of application Ser. No. 172,583, filed Aug. 17, 1971, now U.S. Pat. No. 3,772,272, which in turn is a continuation-in-part of application Ser. No. 37,341, filed May 14, 1970, which in turn is a continuation-in-part of application Ser. No. 878,575, filed Nov. 20, 1969, now both abandoned.

The present invention relates to 1-substituted-4,6-diarylpyrimidin-2(1H)-ones and to the preparation thereof. The invention also relates to compositions and methods for utilizing compounds of said type and their pharmaceutical activities.

In accordance with the invention there is provided compounds of the general formula I:

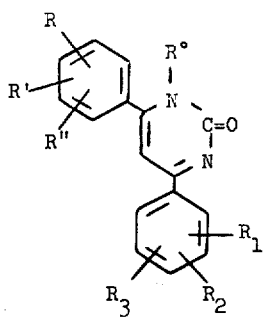

wherein
- R° is lower alkyl of 1 to 5 carbon atoms, e.g. methyl, ethyl and isopropyl,
- each of R and R'' is independently hydrogen, halo of atomic weight of from 19 to 80, lower alkyl of 1 to 3 carbon atoms or lower alkoxy of 1 to 3 carbon atoms,
- R' is hydrogen, halo of atomic weight of from 19 to 80, lower alkyl of 1 to 3 carbon atoms, lower alkoxy of 1 to 3 carbon atoms, nitro or trifluoromethyl,
- each of $R_1$ and $R_3$ is independently hydrogen, halo of atomic weight of from 19 to 80, lower alkyl of 1 to 3 carbon atoms or lower alkoxy of 1 to 3 carbon atoms, and
- $R_2$ is hydrogen, halo of atomic weight of from 19 to 80, lower alkyl of 1 to 3 carbon atoms, lower alkoxy of 1 to 3 carbon atoms, nitro or trifluoromethyl, provided generally that no more than one of R, R' and R'' and no more than one of $R_1$, $R_2$ and $R_3$ is a branched chain hydrocarbon (alkyl and alkoxy) substituent.

A Procedure A for preparing the compounds of formula I involves reacting an appropriately substituted or unsubstituted dibenzoylmethane of formula II:

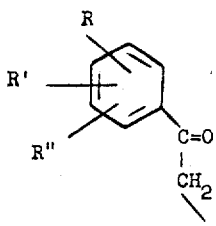

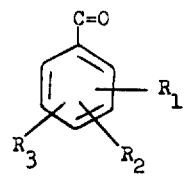

with a compound of formula III:

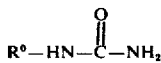

at elevated temperature to obtain a compound of the invention of formula I:

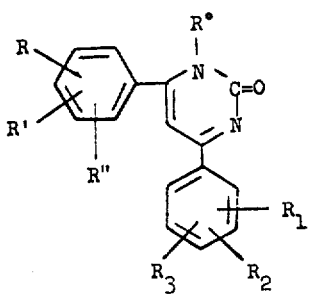

wherein R°, R, R', R'', $R_1$, $R_2$ and $R_3$ are above defined.

An alternate Procedure B for the preparation of the compounds of formula I involves subjecting a compound of the formula IV to oxidation in an organic solvent, said compound of formula IV being represented structurally as follows:

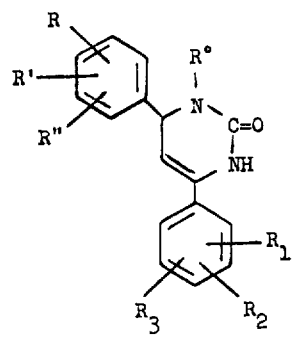

in which R°, R, R', R'', $R_1$, $R_2$ and $R_3$ are as defined.

The preparation of compounds I by Procedure A is conveniently carried out in an organic solvent at elevated temperatures in the range of from 50° to 150°C., preferably 100° to 130°C. and in the presence of an acid as catalyst. The solvent employed is inert with respect to the reactants and product and desirably a polar solvent of conventional type, preferably a lower carboxylic acid of 1 to 3 carbon atoms, more preferably acetic acid. The catalyst employed may be any of several suitable strong acids including both inorganic and organic acids such as hydrogen chloride and p-toluenesulfonic acid, preferably hydrogen chloride. The reaction product of formula I may be isolated from the reaction mixture of Procedure A by working up by established procedures. In situations in which any substituents on the 4-phenyl and 6-phenyl moieties are different or differently placed it will be evident that reaction product will be a mixture of the compounds of formula I. Such mixtures may be separated to recover the individual products of formula I by conventional procedures.

The preparation of compounds I from compounds IV by the reaction of Procedure B may be conveniently carried out in an inert organic solvent at temperature in the range of 0° to 150°C. The oxidizing agents which may be employed are of known type suitable for converting an organic amino moiety to an imino moiety. Representative of such oxidizing agents are the alkali metal permanganates, such as sodium or potassium permanganate, manganese dioxide and mercuric acetate, preferably manganese dioxide. The preferred temperature range when employing an alkali metal permanganate is 10°–30°C. and the preferred range when employing manganese dioxide is 80°–150°C. The organic solvent may be any of several conventional organic solvents including by way of illustration the aromatic solvents, e.g. benzene and the ethers including the cyclic ethers, e.g. dioxane. The reaction product of formula I may be isolated from the Procedure B reaction by working up by established procedures.

The compounds of formulae II and III employed in Procedure A are either known or may be prepared from known materials by conventional procedures.

The compounds of formula IV are preferably prepared in a two step Procedure C involving reaction in a Step 1 a chalcone of the formula V:

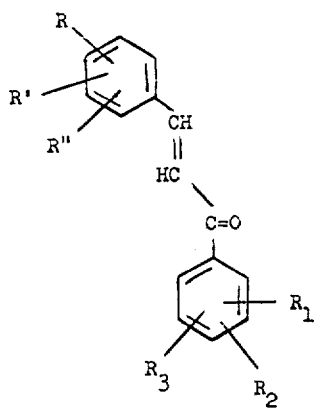

wherein R, R', R'', $R_1$, $R_2$ and $R_3$ are as defined, with an alkylamine of the formula VI:

   VI wherein R° is as defined, and reacting in a Step 2 the resulting product with isocyanic acid of the formula VII:

   VII in an organic solvent to obtain said compound of formula IV.

The reaction Step 1 of Procedure C is desirably carried out at temperatures in the range of from minus 20° to plus 35°C., preferably in the range of from plus 10° to 30°C., with suitable provision being made when the compound of formula VI is a vaporous material at the reaction temperature, e.g. by conducting the reaction under pressure. The reaction may be carried out employing an excess of the compound VI as solvent medium for the reaction or any of several well known conventional solvents may be suitably employed to provide a solvent medium. The reaction product of Step 1 is a compound of the formula VIII:

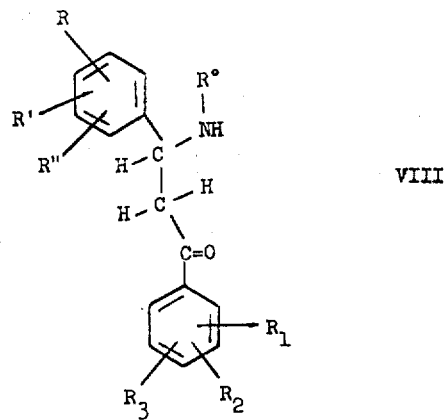

wherein R°, R, R', R'', $R_1$, $R_2$ and $R_3$ are as defined, said compound VIII being relatively unstable at higher temperatures and therefore desirably maintained at lower temperatures below about 35°C. for use in Step 2 of Procedure C.

In Step 2 of Procedure C the reaction product of Step 1 is cyclized by subjecting to reaction with isocyanic acid at temperature in the range of from minus 20° to plus 35°C., preferably in the range of from minus 5° to plus 15°C. The isocyanic acid is known to be unstable and hence is desirably formed in-situ by employing an isocyanate of the formula VII-A:

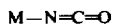   VII-A wherein M is a metal cation displaced in an acidic medium to provide the isocyanic acid, said cation M preferably being a cation of an alkali metal, preferably sodium or potassium; or of an alkaline earth metal, e.g. calcium; or the cation of ammonium. The acid employed to produce the isocyanic acid in-situ is preferably acetic acid which may be also employed as the organic solvent medium for reaction. The compounds of formula IV may be isolated from the Step 2 reaction mixture by working up by established procedures.

The compounds of formulae V and VI employed as starting material in Procedure C are either known per se or may be prepared from known materials by established procedures.

The compounds of general formula I are useful because they possess pharmacological activity in animals. In particular, the compounds of formula I are useful as minor tranquilizers as indicated, for example, by exhibiting a depressant effect in behavior tests in mice and by additionally exhibiting one or more responses from the group of an antagonism of amphetamine in mice, an inhibition of chemically induced seizures in mice and a reinduction of hexobarbital anesthesia in mice. The compounds may also exhibit a CNS depressant effect in other animal tests, for example, by an inhibition of maximal electroshock induced convulsions in mice, by effecting a significant decrease of aggression among shock-induced mice and by effecting a loss of ability of mice to remain on a rotating rod. For such use the dosage of compound I will of course vary depending upon known factors such as the particular compound used and mode of administration. However, in general, satisfactory results may be obtained when administered at a daily dosage of from 1 to 300 milligrams per kilograms of body weight, preferably given in divided doses 2 to 4 times a day or in sustained release form. For most mammals the administration of from 60 to 2000 milligrams of a compound of formula I per day provides satisfactory results and dosages forms suitable for internal administration comprise from about 15 to 1000 milligrams of the compound in admixture with a solid or liquid pharmaceutical carrier or diluent.

Many of the compounds of the formula I are also useful as anti-inflammatory agents as indicated, for example, by the Carrageenan induced edema test in rats on oral administration. Such activity in general is exhibited by the compounds of formula I in which each of R, R', R'', $R_1$, $R_2$ and $R_3$ is hydrogen and also, for example, the specific compounds of Examples 2 and 5d. For such use the dosage of compounds I will of course vary depending upon known factors such as the particular compound used and mode of administration. However, in general, satisfactory results may be obtained when administered at a daily dosage of from 2 to 200 milligrams per kilograms of body weight, preferably given in divided doses 2 to 4 times a day or in sustained release form. For most mammals the administration of from 120 to 2000 milligrams of a compound of formula I per day provides satisfactory results and dosage forms suitable for internal administration comprise from about 30 to 1000 milligrams of the compound in admixture with a solid or liquid pharmaceutical carrier or diluent.

In addition, the compounds of formula I are also useful as sleep-inducers as indicated by sleep studies in cats having chronically implanted electrodes. For such use of the compounds of formula I as sleepinducers satisfactory results may be obtained in general on administration at a dose of from 2 to 300 milligrams per kilograms of body weight. For most larger mammals the administration of a single dose of 120 to 2000 milligrams of a compound of formula I provides satisfactory results and is typically administered at bedtime in admixture with a solid or liquid pharmaceutical carrier or diluent. A particularly preferred sleepinducer of the formula I is the compound 1-ethyl-4,6-diphenyl-pyrimidin-2(1H)-one.

For the above uses, the pharmaceutically useful compounds provided by the invention may be formulated in a conventional manner to contain an effective dose of one or more of said compounds as active ingredient together with one or more conventional ingredients including an inert pharmaceutically acceptable carrier adapted to provide a composition suitable for either oral administration or for administration parenterally in the form of an injectable solution or suspension. In general, the preferred compositions are those adapted for oral administration and conventional forms for this purpose are suitable, such as tablets, dispersible powders, granules, capsules, syrups, elixirs and the like. Such compositions for oral administration may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g. inert diluents such as calcium carbonate, sodium carbonate, lactose and talc, granulating and disintegrating agents, e.g. starch and alginic acid, binding agents, e.g. starch, gelatin and acacia, and lubricating agents, e.g. magnesium stearate, stearic acid and talc. The tablets may be uncoated or coated by known techniques to delay disintegration and adsorption in the gastro-intestinal tract and thereby provide a sustained reaction over a longer period. Similarly, suspensions, syrups and elixirs may contain the active ingredient in admixture with any of the conventional excipients utilized for the preparation of such compositions, e.g. suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g. calcium carbonate, calcium phosphate and kaolin. The preferred pharmaceutical compositions from the standpoint of preparation and ease of administration are solid compositions, particularly hard-filled capsules and tablets.

A representative formulation for oral administration at bedtime to induce sleep is a tablet prepared by conventional tabletting techniques and containing the following ingredients:

| Ingredient | Weight (mg.) |
| --- | --- |
| 1-ethyl-4,6-phenyl-pyrimidin-2(1H)-one | 200 |
| Tragacanth | 10 |
| Lactose | 147.5 |
| Corn Starch | 25 |
| Talcum | 15 |
| Magnesium Stearate | 2.5 |

The following examples show representative compounds encompassed within the scope of this invention and the manner in which such compounds are prepared. However, it is to be understood that the examples are for purposes of illustration only.

EXAMPLE 1

1-Methyl-4,6-diphenyl-pyrimidin-2(1H)-one

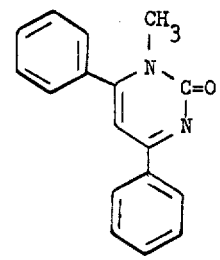

A solution of 15 g. of dibenzoylmethane and 43.5 g. of M-methylurea in 250 ml. of glacial acetic acid is refluxed for 8 hours while dry hydrogen chloride gas is bubbled through the reaction mixture. An additional amount of 5 equivalents of N-methylurea is then added and refluxing continued for another 8 hours while bubbling hydrogen chloride through the reaction system. The N-methylurea addition is again repeated and refluxing procedure continued for a further 8 hours. The resulting mixture is filtered and the filtrate evaporated in vacuo to dryness. The residue is taken up with methylene chloride, treated with 2N. sodium hydroxide and the methylene chloride layer separated. The aqueous layer is extracted three times with methylene chloride. All methylene chloride fractions are combined and extracted several times with water, dried, filtered and evaporated in vacuo to dryness. The residue is crystallized from methylene chloride/diethyl ether to obtain 1-methyl-4,6-diphenylpyrimidin-2(1H)-one, m.p. 183°–185°C.

EXAMPLE 2

1-Methyl-4,6-di(m-chlorophenyl)-pyrimidin-2(1H)-one

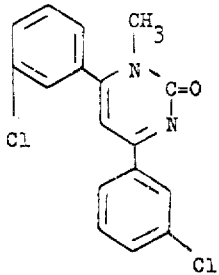

To a solution of 38 g. di(m-chlorobenzoyl)methane in 400 ml. glacial acetic acid is added 23 g. N-methylurea and 57 g. p-toluene sulfonic acid. This mixture is refluxed for 24 hours and acetic acid removed by evaporation in vacuo. The residue is treated with 2N. sodium hydroxide till basic, extracted several times with methylene chloride. The combined methylene chloride extracts are then exhaustively extracted with water, dried and evaporated in vacuo to dryness. The residue is crystallized from methylene chloride/diethyl ether and then twice from benzene to obtain 1-methyl-4,6-di(m-chlorophenyl)-pyrimidine-2(1H)-one, m.p. 178°–181°C.

EXAMPLE 3

Following the general procedure of the preceding Examples 1 and 2 the following compounds of the invention are prepared:

a. 1-ethyl-4,6-diphenyl-pyrimidin-2(1H)-one, m.p. 142°–144°C.
(Crystallization from methylene chloride/diethyl ether).

b. 1-n-butyl-4,6-diphenyl-pyrimidin-2(1H)-one, m.p. 123°–125°C.
(Crystallization from methylene chloride/diethyl ether).

c. 1-ethyl-4,6-di(m-bromophenyl)-pyrimidin-2(1H)-one, m.p. 144°–146°C.
(Crystallization from methylene chloride/diethyl ether).

d. 1-n-propyl-4,6-diphenyl-pyrimidin-2( 1H)-one, m.p. 169°–172°C.
(Crystallization from methylene chloride/diethyl ether).

e. 1-methyl-4,6-di(m-methylphenyl)-pyrimidin-2(1H)-one, m.p. 151°–152°C.
(Crystallization from methylene chloride/diethyl ether).

EXAMPLE 4

1-Methyl-4-phenyl-6-(3',4'-dimethoxy)phenyl-pyrimidin-2(1H)-one.

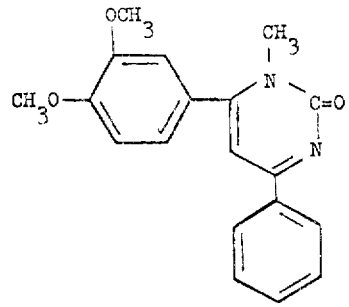

STEP A: Preparation of 1-methyl-4-phenyl-6-(3',4'-dimethoxy)phenyl-3,4-dihydropyrimidin-2(1H)-one A solution of 20 g. of 3,4-dimethoxychalcone in a large excess methylamine is stirred at room temperature in a steel bomb overnight. The methylamine is then removed in vacuo at bath temperature regulated below 25°C. The oily residue is then dissolved with ice bath cooling in 200 ml. of glacial acetic acid and to this solution is added 5 equivalents of potassium cyanate. The reaction mixture is stirred at ice bath temperature 2 to 3 hours and then left overnight with stirring at room temperature. Next day the reaction mixture is evaporated in vacuo, the residue treated with water and extracted with ethyl acetate. The combined ethyl acetate extracts after washing with water is dried over sodium sulfate and evaporated in vacuo. The residue is crystallized from methylene chloride/diethyl ether to obtain 1-methyl-4-phenyl-6-(3',4'-dimethoxy)phenyl-3,4-dihydropyrimidin-2(1H)-one, m.p. 163°–165°C.

STEP B: Preparation of 1-methyl-4-phenyl-6-(3',4'-dimethoxy)phenylpyrimidin-2(1H)-one A mixture of 6.0 g. of 1-methyl-4-phenyl-6-(3',4'-dimethoxy)phenyl-3,4-dihydropyrimidin-2(1H)-one, 6 g. of activated manganese dioxide and 250 ml. of xylene is refluxed for 48 hours, the resulting mixture filtered while hot and then cooled to obtain a solid material which is collected and crystallized from methylene chloride/diethyl ether to obtain 1-methyl-4-phenyl-6-(3',4'-dimethoxy)phenyl-pyrimidin-2(1H)-one, m.p. 217°–219°C.

EXAMPLE 5

Following the general procedure of Example 4 the following compounds of the invention are prepared:

a. 1-methyl-4-phenyl-6-(3',4'-dichlorophenyl)-pyrimidin-2(1H)-one, m.p. 248°–250°C.
(Crystallization from methylene chloride/diethyl ether).

b. 1-isopropyl-4,6-diphenyl-pyrimidin-2(1H)-one, m.p. 156°–158°C.
(Crystallization from methylene chloride/diethyl ether).

c. 1-methyl-4-phenyl-6-(m-nitrophenyl)-pyrimidin-2(1H)-one, m.p. 221°–223°C.

(Crystallization from methylene chloride/diethyl ether).

d. 1-methyl-4-phenyl-6-(p-methoxyphenyl)-pyrimidin-2(1H)-one, m.p. 160°–165°C.
(Crystallization from methylene chloride/diethyl ether).

e. 1-methyl-4-phenyl-6-(2',6'-dichlorophenyl)-pyrimidin-2(1H)-one, m.p. 180°–182°C.
(Crystallization from diethyl ether/petroleum ether).

f. 1-ethyl-4-phenyl-6-(3',4'-dimethoxyphenyl)-pyrimidin-2(1H)-one, m.p. 194°–196°C.
(Crystallization from methylene chloride/diethyl ether).

g. 1-ethyl-4-(3',4'-dichlorophenyl)-6-phenyl-pyrimidin-2(1H)-one, m.p. 206°–209°C.
(Crystallization from methylene chloride/diethyl ether).

h. 1-ethyl-4-(m-methoxyphenyl)-6-(m-nitrophenyl)-pyrimidin-2(1H)-one, m.p. 159°–161°C.
(Crystallization from methylene chloride/diethyl ether).

i. 1-ethyl-4-(m-nitrophenyl)-6-(m-methoxyphenyl)-pyrimidin-2(1H)-one, m.p. 206°–206°C.
(Crystallization from methylene chloride/diethyl ether).

What is claimed is:

1. The method of tranquilizing a mammal comprising administering to a mammal in need of tranquilization a tranquilizing effective amount of a compound of the formula:

wherein
$R^\circ$ is alkyl of 1 to 5 carbon atoms,
each of R and R" is independently hydrogen, fluoro, chloro, bromo, alkyl of 1 to 3 carbon atoms or alkoxy of 1 to 3 carbon atoms,
R' is hydrogen, fluoro, chloro, bromo, alkyl of 1 to 3 carbon atoms, alkoxy of 1 to 3 carbon atoms, nitro or trifluoromethyl,
each of $R_1$ and $R_3$ is independently hydrogen, fluoro, chloro, bromo, alkyl of 1 to 3 carbon atoms or alkoxy of 1 to 3 carbon atoms, and
$R_2$ is hydrogen, fluoro, chloro, bromo, alkyl of 1 to 3 carbon atoms, alkoxy of 1 to 3 carbon atoms, nitro or trifluoromethyl, provided that no more than one of R, R' and R" and no more than one of $R_1$, $R_2$ and $R_3$ is a branched chain substituent.

2. The method of claim 1 in which each of R" and $R_3$ is hydrogen.

3. The method of claim 2 in which each of $R_1$ and $R_2$ is hydrogen.

4. The method of claim 2 in which each of R and R' is hydrogen.

5. The method of claim 1 in which the compound is administered at a daily dose of from 60 to 2000 milligrams.

* * * * *